United States Patent [19]

Niedballa et al.

[11] 4,269,847

[45] May 26, 1981

[54] ANTIINFLAMMATORY-4,5-DIPHENYL-2-SUBSTITUTED-THIO-IMIDAZOLES AND THEIR CORRESPONDING SULFOXIDES AND SULFONES

[75] Inventors: Ulrich Niedballa; Irmgard Böttcher, both of Berlin, Fed. Rep. of Germany

[73] Assignee: Schering Aktiengesellschaft, Berlin and Bergkamen, Fed. Rep. of Germany

[21] Appl. No.: 41,367

[22] Filed: May 22, 1979

[30] Foreign Application Priority Data

May 24, 1978 [DE] Fed. Rep. of Germany ....... 2823197

[51] Int. Cl.³ ................. A61K 31/415; C07D 233/84
[52] U.S. Cl. .......................... 424/273 R; 548/336; 548/337; 546/256; 424/263; 424/275; 424/285; 260/347.2; 549/78
[58] Field of Search ................. 548/337; 424/273 R

[56] References Cited

U.S. PATENT DOCUMENTS

| | | | |
|---|---|---|---|
| 3,488,423 | 1/1970 | Doebel | 548/337 |
| 3,636,003 | 1/1972 | Doebel et al. | 548/337 |
| 3,651,080 | 3/1972 | Doebel et al. | 548/337 |
| 3,842,097 | 10/1974 | Tweit | 548/337 |
| 3,915,980 | 10/1975 | Gebert et al. | 548/337 |
| 4,159,338 | 6/1979 | Cherkofsky et al. | 548/337 |

FOREIGN PATENT DOCUMENTS 2635876 3/1977 Fed. Rep. of Germany .

OTHER PUBLICATIONS

Bhatt et al., Current Science, vol. 17, 1948, pp. 184–185.

*Primary Examiner*—Henry R. Jiles
*Assistant Examiner*—Jane T. Fan
*Attorney, Agent, or Firm*—Millen & White

[57] ABSTRACT

Imidazole derivatives of the formula

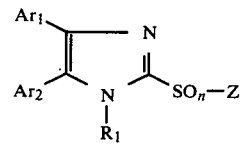

wherein

Ar$_1$ and Ar$_2$ are each phenyl; phenyl substituted by halogen, C$_{1-4}$ alkyl, C$_{1-4}$ alkoxy or C$_{2-6}$ dialkylamino; pyridyl; furyl; or thienyl; with the proviso that Ar$_1$ and Ar$_2$ are not both unsubstituted phenyl;

R$_1$ is hydrogen, C$_{1-4}$ alkyl or C$_{1-4}$ alkyl substituted by hydroxy, C$_{1-4}$ alkoxy or C$_{1-6}$ alkanoyloxy;

n is 0, 1 or 2; and

Z is a C$_{2-6}$-alkyl or -alkenyl residue substituted by one or two of hydroxy, C$_{1-4}$ alkoxy, C$_{2-8}$ alkylenedioxy, C$_{1-6}$ alkanoyloxy or benzoyloxy, or by one alkoxycarbonyl group;

and the salts thereof with physiologically acceptable acids, possess valuable pharmacological properties.

24 Claims, No Drawings

ANTIINFLAMMATORY-4,5-DIPHENYL-2-SUBSTITUTED-THIO-IMIDAZOLES AND THEIR CORRESPONDING SULFOXIDES AND SULFONES

BACKGROUND OF THE INVENTION

The present invention relates to novel imidazole derivatives, a process for their preparation and pharmaceutical preparations containing them as the active ingredients.

SUMMARY OF THE INVENTION

It is an object of this invention to provide new imidazoles having pharmacological effectiveness.

Upon further study of the specification and appended claims, further objects and advantages of this invention will become apparent to those skilled in the art.

These objects have been attained by providing imidazoles of formula I

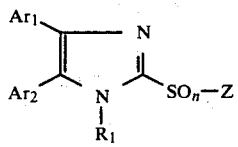

wherein $Ar_1$ and $Ar_2$ are each phenyl; phenyl substituted by halogen, $C_{1-4}$ alkyl, $C_{1-4}$ alkoxy or $C_{2-6}$ dialkylamino; pyridyl; furyl; or thienyl; with the proviso that $Ar_1$ and $Ar_2$ are not both unsubstituted phenyl;

$R_1$ is hydrogen, $C_{1-4}$ alkyl or $C_{1-4}$ alkyl substituted by hydroxy, $C_{1-4}$ alkoxy or $C_{1-6}$ alkanoyloxy;

n is 0, 1 or 2; and

Z is a $C_{2-6}$-alkyl or -alkenyl residue substituted by one or two of hydroxy, $C_{1-4}$ alkoxy, $C_{2-8}$ alkylenedioxy, $C_{1-6}$ alkanoyloxy or benzoyloxy, or by one alkoxycarbonyl group;

and the salts thereof with physiologically acceptable acids.

DETAILED DISCUSSION

According to this invention, the substituents $Ar_1$ and $Ar_2$ of the imidazole derivatives are each phenyl optionally substituted by halogen (F, Cl, Br, I), alkyl, alkoxy or dialkyl-amino; pyridyl; furyl; or thienyl. Suitable phenyl residues $Ar_1$ and $Ar_2$ substituted by halogen atoms include, for example, mono- or difluorophenyl and mono- or dichlorophenyl, and, in particular, para-fluorophenyl or para-chlorophenyl. Alkyl-substituted phenyl residues include, preferably, those having alkyl groups of 1-4 carbon atoms (for example, methyl, ethyl, propyl or isopropyl groups). Phenyl residues substituted by alkoxy groups include, preferably, those having alkoxy groups of 1-4 carbon atoms, (e.g., methoxy, ethoxy, propoxy or isopropoxy groups). Phenyl residues substituted by dialkylamino groups include, preferably, those having dialkylamino residues of 2-6 total carbon atoms; for example, dimethylamino, methylethylamino or diethylamino. Preferably, 1-2 substituents can be included on each phenyl nucleus.

The substituents $Ar_1$ and $Ar_2$ can be alike or different providing that both substituents are not unsubstituted phenyl.

$R_1$ is hydrogen or alkyl of 1-4 carbon atoms optionally substituted by hydroxy groups, alkoxy groups or acyloxy groups. Preferably, the substituent $R_1$ represents an unsubstituted alkyl group or an alkyl group substituted in the 2-position by an hydroxy group, by an alkoxy group of 1-4 carbon atoms (e.g., methoxy, ethoxy, propoxy or isopropoxy) or by an alkanoyloxy group of 1-6 carbon atoms (e.g., formyloxy, acetoxy, propionyloxy, or butyryloxy). In particular, the substituent $R_1$ may be hydrogen or methyl.

The substituent Z can be an unsaturated or preferably saturated, preferably aliphatic acyclic hydrocarbon residue of 2-6 carbon atoms substituted by one or two of the following groups: hydroxy groups, alkoxy groups, alkylenedioxy groups or acyloxy groups, or by one alkoxycarbonyl group. The unsubstituted hydrocarbon moiety, thus, generally is a residue of an alkane or alkene or equivalents thereof. Preferably, the Z hydrocarbon residue is of 1-3 carbon atoms, most preferably a $C_{1-3}$ alkyl residue, and especially ethyl.

Suitable alkoxy groups of substituent Z (including those on the alkoxycarbonyl group) preferably contain 1-4 carbon atoms, e.g., methoxy, ethoxy, propoxy, isopropoxy, butoxy, or tert-butoxy. Suitable $C_{2-8}$ alkylenedioxy groups of substituent Z include those wherein the dioxy portion is connected to the Z hydrocarbon residue, e.g., preferably alkylenedioxy groups of 2-6 total carbon atoms, including any pendant alkyl groups such as, for example, the 1,2-ethylenedioxy group, the 1,3-propylenedioxy group or the 2,2-dimethylpropylenedioxy group; as well as those wherein the dioxy portion is not connected to the Z hydrocarbon residue, e.g., preferably, 1,3-dioxolan-2-yl or di-$C_{1-4}$-alkoxy methylene. Suitable acyloxy groups of substituent Z include preferably those groups derived from an aliphatic, preferably saturated carboxylic acid of 1-6 carbon atoms, such as formic acid, acetic acid, propionic acid, butyric acid, isobutyric acid, trimethylacetic acid, valeric acid, etc. (i.e., $C_{1-6}$ alkanoyloxy) or from benzoic acid. Equivalents of all these groups are also included.

The substituents of residue Z are preferably in the 2- or 3-position of the hydrocarbon residue. Preferably, the total number of all substituents on any Z residue is 1-2.

Especially preferred compounds are those wherein substituents $Ar_1$ and $Ar_2$ each are phenyl; phenyl substituted in the para position by fluorine, chlorine, alkyl of 1-4 carbon atoms, alkoxy of 1-4 carbon atoms or dialkylamino of 2-6 carbon atoms; 2-pyridyl; 2-furfuryl; or 2-thienyl; e.g., phenyl, 4-fluorophenyl, 4-chlorophenyl, 4-methylphenyl, 4-methoxyphenyl, 4-dimethylaminophenyl, 2-pyridyl or 2-thienyl; and/or wherein the substituent Z is a $C_{2-6}$-alkyl or -alkenyl residue substituted by one or two hydroxy groups attached to different carbon atoms; by $C_{1-4}$ alkoxy; by $C_{1-6}$ alkanoyloxy or by benzoyloxy; e.g., 2-hydroxyethyl; e.g., a $C_{1-3}$-alkyl or -alkenyl residue substituted by 1,3-dioxaolan-2-yl or by a dialkoxymethylene group of 1-4 carbon atoms in each alkoxy group; e.g., a $C_{1-3}$-alkyl or -alkenyl residue substituted by a $C_{1-4}$ alkoxycarbonyl group.

Physiologically acceptable salts of the imidazole derivatives of formula I include, for example, the salts of hydrogen chloride, hydrogen bromide, or hydrogen iodide; of sulfuric acid or phosphoric acid; or salts of organic acids, such as formic acid, acetic acid, succinic acid, maleic acid, tartaric acid or citric acid.

The novel imidazole derivatives of formula I can be prepared by following fully conventional methods such as those outlined below. These can be conducted under fully conventional conditions as described, e.g., in Liebigs Annalen 284, 1894: 9 et seq.; J. Chem. Soc. 1931: 3043 et seq.; J. Med. Chem. 20, 1977: 563 et seq.; Liebigs Annalen 214, 1882: 257 et seq.; J. Chem. Soc. 1942: 232 et seq.; J. Chem. Soc. 1963: 2195 et seq. Houben-Weyl: "Methoden der organischen Chemie" [Methods of Organic Chemistry] vol. IX: 229 et seq.; Bull. Soc. France 1977: 271 et seq.; and DOS No. 2,635,876.

Typical processes for preparing the imidazole derivatives of formula I include those wherein, in a conventional manner:

(a) an imidazole derivative of formula II

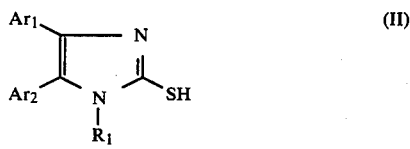

wherein $Ar_1$, $Ar_2$ and $R_1$ are as defined above, is condensed with a compound of formula III

WZ    (III)

wherein

Z is as defined above and

W is a halogen atom, an alkylsulfonyloxy residue or an arylsulfonyloxy residue;

or (b) for the preparation of imidazole derivatives of Formula I wherein Z is

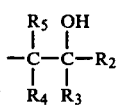

wherein $R_2$, $R_3$, $R_4$ and $R_5$ are hydrogen atoms or hydrocarbon residues of, in total, 1–4 carbon atoms optionally substituted by hydroxy, alkoxy, alkylenedioxy or acyloxy, an epoxide of formula IV

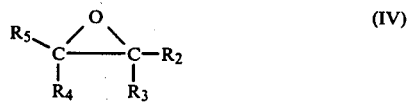

wherein $R_2$, $R_3$, $R_4$ and $R_5$ are as defined above, is added chemically to an imidazole derivative of formula II;

or (c) for the preparation of imidazole derivatives of formula I wherein Z is

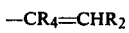

wherein $R_2$ and $R_4$ are as defined above, an ethynyl compound of formula V

    (V)

wherein $R_2$ and $R_4$ are as defined above, is chemically added to an imidazole derivative of formula II;

and optionally the thio compounds of formula I obtained according to process variations (a) through (c) are oxidized to the corresponding sulfinyl compounds or sulfonyl compounds;

optionally the alkoxycarbonyl compounds obtained according to process variations (a) through (c) are reduced to the corresponding hydroxymethyl compounds;

imidazole derivatives unsubstituted in the 1-position are alkylated;

imidazole derivatives containing hydroxy groups are esterified; and/or imidazole derivatives of formula I are converted into the salts thereof with physiologically acceptable acids.

After the synthesis has been accomplished, the racemic imidazole derivatives of formula I can be split into their optical antipodes by conventional processes, for example, by chromatographing these products by column chromatography on optically active carriers (e.g., "Sephadex").

The starting compounds for the processes of this invention are known or can be prepared by conventional methods (Synthesis 1976: 733 et seq. and Zhur.Obsch.Khim 31, 1961: 1039 et seq.). Such methods for producing these starting compounds are illustrated hereinbelow with reference to several typical compounds:

A solution of 20.43 g. of 4-dimethylaminobenzoin in 250 ml. of dimethylformamide is combined with 12.18 g. of ammonium thiocyanate; the mixture is heated for 14 hours to 80° C. After cooling, the solution is stirred into ice water; the thus-precipitated crystals are vacuum-filtered and recrystallized from hot ethanol, thus obtaining 14.62 g. of 4-(4-dimethylamino)-5-phenyl-2-mercaptoimidazole, m.p. 277°–280° C.

A solution of 4.04 g. of 2-pyridoin in 50 ml. of dimethylformamide is combined with 3.04 g. of ammonium thiocyanate, and the solution is heated for 12 hours to 80° C. After cooling, the solution is stirred into ice water; the thus-precipitated crystals are vacuum-filtered and recrystallized from hot ethanol, thus obtaining 4.70 g. of 4,5-bis-(2-pyridyl)-2-mercaptoimidazole, m.p. 285°–287° C.

A solution of 11.2 g. of 2-thiophenoin in 150 ml. of dimethylformamide is combined with 7.6 g. of ammonium thiocyanate, and the solution is heated for 8 hours to 80° C. After cooling, the solution is stirred into ice water; the thus-precipitated product is vacuum-filtered and recrystallized from hot ethanol, thus obtaining 7.23 g. of 4,5-di(2-thienyl)-2-mercaptoimidazole, m.p. 300°–301° C.

The imidazole derivatives of formula I are distinguished by a pronounced antiinflammatory and antiallergic activity in mammals, including humans. This effect is especially striking in the imidazole derivatives mentioned as preferred above.

Moreover, the imidazole derivatives of formula I are distinguished by exhibiting a very favorable dissociation between desirable pharmacological efficacy and undesirable—especially ulcerogenic—side effects. This dissociation is especially pronounced in those imidazole derivatives of formula I wherein n is 1 or 2.

The antiinflammatory effectiveness of the compounds of this invention can be determined with the aid of the conventional adjuvant arthritis test which is conducted as follows:

Female and male rats of the Lewis strain (LEW) are used and weigh between 110 and 190 g. The animals receive drinking water and pressed feed "Altromin" ad libitum.

For each dose group, 10 rats are employed.

*Mycobacterium butyricum* by Difko, Detroit, is used as the irritant. A suspension of 0.5 mg. of *Mycobacterium butyricum* in 0.1 ml. of thinly fluid paraffin (DAB [German Pharmacopoeia] 7) is injected at a subplantar location into the right hind paw. The test compounds are given orally starting with the 11th day of the test daily over a period of 4 days. The compounds are administered as a clear aqueous solution or as a crystalline suspension with the addition of Myrj 53 (85 mg. %) in an isotonic sodium chloride solution.

Test Setup:

The rats are divided as uniformly as possible with respect to their body weight into various groups. After measuring the volume of the right hind paw by plethysmography, 0.1 ml. of adjuvant is injected into the paw in the subplantar region. The right hind paws are measured from the 14th day of the experiment until the end of the test. The duration of the experiment is 3 weeks.

The healing of the hind paws attained with the predetermined dose is recorded.

A frequent complication in the therapy with non-steroidal antiinflammatory agents is the occurrence of stomach ulcerations. This side effect can be demonstrated by animal experiment, determining at a given dose the number of lesions observed and the total area thereof. The ulcer test is conducted as follows.

Male Wistar rats (SPF) are utilized. The animals are in a weight range of 130±10 g. Sixteen hours prior to commencing the experiment, the animals are put on a fast; they receive water ad libitum.

Per dose, 5 animals are employed. The substances are applied once orally, dissolved in a sodium chloride solution or as a crystalline suspension with the addition of 85 mg. % Myrj 53.

Three hours after administration of the compound, 1 ml. of a 3% solution of the dye pure diphenyl blue is injected intravenously, and the animal is sacrificed. The stomach is resected and examined microscopically with respect to the number and total size of epithelial lesions and ulcers, which are brought out by dye accumulations.

The factor by which the lesions have multiplied in number and the area as compared with the lesions of the correspondingly treated control animals are determined.

The following table shows the results obtained in these tests with the compound of this invention as compared with the previously known compound indomethacin (compound 1) and with the structurally analogous compounds 2 and 3 known from DOS [German Unexamined Laid-Open Application] No. 2,635,876.

TABLE

| No. | Compound | Adjuvant Arthritis Test | | Ulcus Test | | |
|---|---|---|---|---|---|---|
| | | Dose in mg./kg. Animal | % Healing of Right Hind Paws | Dose in mg./kg. Animal | Factor for | |
| | | | | | Number | Area |
| 1 | Indomethacin | 4 × 4 mg. | 48–58% | 8 mg. | over 20 | over 30 |
| 2 | 4,5-Bis(4-methoxyphenyl)-2-ethylthioimidazole | 4 × 50 mg. | 46% | 200 mg. | 13.5 | 30 |
| 3 | 4,5-Bis(4-methoxyphenyl)-2-ethylsulfonylimidazole | 4 × 50 mg. | 53% | 200 mg. | 4.5 | 4.5 |
| 4 | 4,5-Bis(4-methoxyphenyl)-2-(2-hydroxyethylthio)-imidazole | 4 × 50 mg. | 45% | 200 mg. | 4.4 | 8.7 |
| 5 | 4,5-Bis(4-methoxyphenyl)-2-(2-hydroxyethylsulfinyl)imidazole | 4 × 50 mg. | 52% | 200 mg. | 1.0 | 1.0 |
| 6 | 4,5-Bis(4-methoxyphenyl)-2-(2-hydroxyethylsulfonyl)imidazole | 4 × 50 mg. | 51% | 200 mg. | 1.2 | 1.2 |
| 7 | 4,5-Bis(4-chlorophenyl)-2-(2-hydroxyethylsulfonyl)imidazole | 4 × 50 mg. | 49% | 200 mg. | 0.5 | 0.5 |
| 8 | 4,5-Bis(4-methoxyphenyl)-2-(2,2-dimethoxyethylsulfonyl)-imidazole | 4 × 50 mg. | 49% | 200 mg. | 2.6 | 2.3 |
| 9 | [4,5-Bis(4-methoxyphenyl)-2-imidazolyl]-(1,3-dioxolan-2-yl-methyl)sulfone | 4 × 50 mg. | 45% | 200 mg. | 1.8 | 1.8 |

Surprisingly, there are, among the compounds of this invention, also those possessing in addition to the antiinflammatory efficacy also a pronounced antiulcerogenic and tumor-inhibiting effectiveness.

Thus, rats receiving, in addition to 8 mg./kg. of body weight of 4,5-bis(4-methoxyphenyl)-2-(2-hydroxyethylsulfinyl)-imidazole show stomach lesions which are significantly reduced in number and area as compared with a corresponding control group wherein only indomethacin was administered.

On the other hand, a dose of 50 mg./kg. of animal of bis(4-methoxyphenyl)-2-(2-hydroxyethylsulfinyl)imidazole can significantly suppress tumor formation in rats infected with 100,000 Ehrlich tumor cells.

Accordingly, the novel compounds are suitable, in combination with the vehicles customary in galenic pharmacy, for example, for the treatment of acute and chronic polyarthritis, neurodermitis, bronchial asthma, hay fever, etc.

The specialty drug preparations are produced in the usual way by converting the active agents with suitable additives, vehicles, and flavor ameliorating substances into the desired forms of application, such as tablets, dragees, capsules, solutions, inhalants, etc.

In particular, suitable for oral application are tablets, dragees, and capsules containing, for example, 1–250 mg. of active ingredient and 50 mg. to 2 g. of pharmacologically inert carriers, e.g., lactose, amylose, talc, gelatin, magnesium stearate, and similar materials, as well as the customary additives. Typical dosages are 1–500 mg./kg. of body weight/day for use as an antiinflammatory agent. The administration is fully conventional, e.g., in analogy to that for indomethacin.

The pharmacologically active compounds of Formula I can be processed in accordance with conventional methods of galenic pharmacy to provide medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

The specialty drugs are conventionally prepared by formulating the active agents together with suitable additives into the desired form for administration. In the thus-formulated medicinal agents, the effective agent concentration is dependent on the compound used and the form of application and can be easily determined by clinical tests under conventional considerations.

Without further elaboration, it is believed that one skilled in the art can, using the preceding description, utilize the present invention to its fullest extent.

The following preferred specific embodiments are, therefore, to be construed as merely illustrative, and not limitative of the remainder of the disclosure in any way whatsoever.

The temperatures hereinbelow are degrees Celsius.

EXAMPLE 1

A mixture of 6.24 g. of 4,5-bis(4-methoxyphenyl)-2-mercaptoimidazole and 3.0 g. of 2-bromoethanol in 100 ml. of absolute ethanol is refluxed for 4 hours under exclusion of moisture and an argon atmosphere. The solution, cooled to 5°, is neutralized by adding 2 N sodium hydroxide solution, poured into 900 ml. of ice water, and allowed to stand at ice bath temperature until crystallization has been completed. After 45 minutes the crystals are removed by vacuum-filtering, washed with ice water, and dried under vacuum at 70°. The crude product is recrystallized from 250 ml. of ethyl acetate with the addition of a small amount of activated carbon, thus obtaining 5.38 g. of 4,5-bis(4-methoxyphenyl)-2-(2-hydroxyethylthio)imidazole as colorless crystals, m.p. 182°.

EXAMPLE 2

3.30 g. of 3-chloroperbenzoic acid, dissolved in 150 ml. of dichloromethane, is added dropwise to a solution of 5.34 g. of 4,5-bis(4-methoxyphenyl)-2-(2-hydroxyethylthio)-imidazole in 1.25 l. of dichloromethane. The solution is stirred for 24 hours at room temperature and then washed with saturated sodium bicarbonate solution. The organic solution is separated and dried over sodium sulfate, whereupon it is concentrated under vacuum. The residue is crystallized from 30 ml. of dioxane with the addition of a small quantity of activated carbon, thus obtaining 3.01 g. of 4,5-bis(4-methoxyphenyl)-2-(2-hydroxyethylsulfinyl)imidazole, m.p. 184°.

EXAMPLE 3

2.70 g. of 3-chloroperbenzoic acid, dissolved in 120 ml. of dichloromethane, is added dropwise to a solution of 2.14 g. of 4,5-bis(4-methoxyphenyl)-2-(2-hydroxyethylthio)-imidazole in 450 ml. of dichloromethane. The mixture is stirred for 4 hours at room temperature, washed with saturated sodium bicarbonate solution, the organic phase is separated, dried over sodium sulfate, and concentrated under vacuum. The oily residue is recrystallized from 150 ml. of cyclohexane/ether 1:1, thus obtaining 1.68 g. of 4,5-bis(4-methoxyphenyl)-2-(2-hydroxyethylsulfonyl)imidazole, m.p. 168°.

EXAMPLE 4

A solution of 7.13 g. of 4,5-bis(4-methoxyphenyl)-2-(2-hydroxyethylthio)imidazole in 100 ml. of absolute ethanol, wherein 600 mg. of sodium was dissolved, is combined with 3.73 g. of methyl iodide in 20 ml. of absolute ethanol. The solution is heated for 20 minutes under argon with refluxing. After cooling, the solution is poured into 1500 ml. of ice water, neutralized with 2 N hydrochloric acid, and extracted with chloroform. The organic phase is dried over sodium sulfate and concentrated under vacuum. The crude product is recrystallized from 100 ml. of ethanol with the addition of a small amount of activated carbon from 1000 ml. of diisopropyl ether, thus producing 4.29 g. of 4,5-bis(4-methoxyphenyl)-2-(2-hydroxyethylthio)-1-methylimidazole, m.p. 127°.

EXAMPLE 5

Under the exclusion of moisture, a solution of 1.43 g. of acetoxyacetyl chloride in 50 ml. of absolute tetrahydrofuran is added dropwise at 10° to a solution of 3.57 g. of 4,5-bis(4-methoxyphenyl)-2-(2-hydroxyethylthio)imidazole in 100 ml. of absolute tetrahydrofuran. After 30 minutes, the reaction mixture is evaporated to dryness under vacuum, the residue is recrystallized from absolute ethanol, the thus-precipitated crystals are washed with alcohol and absolute ether, and dried under vacuum at 50°, thus obtaining 3.27 g. of O-acetylglycolic acid {2-[4,5-bis(4-methoxyphenyl)-2-imidazolylthio]ethyl}ester, hydrochloride, m.p. 148°–150°.

EXAMPLE 6

3.13 g. of 4,5-bis(4-methoxyphenyl)-2-hydroxyethylmercapto-imidazole is heated under reflux in a mixture of 10 ml. of glacial acetic acid and 20 ml. of acetic anhydride for 2 hours. The solvent is removed under vacuum. The residue is freed of any remaining acetic anhydride by codistillation with ethanol. The mixture is again taken up in ethanol, clarified with activated carbon, and after evaporation of the solvent the product is 2.95 g. of 4,5-bis(4-methoxyphenyl)-2-(2-acetoxyethylthio)imidazole as a colorless oil.

$C_{21}H_{22}N_2O_4S$ (398.484): Calculated: C: 63.30; H: 5.57; N: 7.03; S: 8.05. Found: C: 63.42; H: 5.69; N: 6.90; S: 7.92.

EXAMPLE 7

A mixture of 8.65 g. of 4,5-bis(4-fluorophenyl)-2-mercaptoimidazole and 4.97 g. of 2-bromoethanol in 150 ml. of absolute ethanol is heated under argon for 4 hours under reflux. The cooled solution is neutralized with 2 N sodium hydroxide solution, poured into 800 ml. of ice water, and left for 45 minutes at ice bath temperature. The crude product is vacuum-filtered, washed with water, and dried under vacuum at 70°. The crude product is then recrystallized from 175 ml. of ethyl acetate with the addition of a small amount of activated carbon, thus obtaining 6.76 g. of 4,5-bis(4-fluorophenyl)-2-(2-hydroxyethylthio)imidazole, m.p. 192°.

EXAMPLE 8

Under the conditions of Example 2, 0.5 g. of 4,5-bis(4-fluorophenyl)-2-(2-hydroxyethylthio)imidazole is oxidized, thus obtaining 0.24 g. of 4,5-bis(4-fluorophenyl)-2-(2-hydroxyethylsulfinyl)imidazole, m.p. 182°.

EXAMPLE 9

Under the conditions of Example 3, 0.6 g. of 4,5-bis(4-fluorophenyl)-2-(2-hydroxyethylthio)imidazole is oxidized, thus obtaining 4,5-bis(4-fluorophenyl)-2-(2-hydroxyethylsulfonyl)imidazole, m.p. 167°.

EXAMPLE 10

A mixture of 8.03 g. of 4,5-bis(4-chlorophenyl)-2-mercaptoimidazole and 4.14 g. of 2-bromoethanol in 125 ml. of absolute ethanol is heated under argon for 4 hours with reflux. The cooled solution is neutralized with 2 N sodium hydroxide solution, poured into 1200 ml. of ice water, and left at ice bath temperature for 45 minutes. The crystals are vacuum-filtered, washed with water, and dried under vacuum at 60°. The crude product is recrystallized from 500 ml. of acetonitrile with the addition of a small amount of activated carbon, thus producing 8.76 g. of 4,5-bis(4-chlorophenyl)-2-(2-hydroxyethylthio)imidazole, m.p. 202°.

EXAMPLE 11

Under the conditions of Example 2, 0.5 g. of 4,5-bis(4-chlorophenyl)-2-(2-hydroxyethylthio)imidazole is oxidized, thus obtaining 0.38 g. of 4,5-bis(4-chlorophenyl)-2-(2-hydroxyethylsulfinyl)imidazole, m.p. 186°.

EXAMPLE 12

Under the conditions of Example 3, 0.5 g. of 4,5-bis(4-chlorophenyl)-2-(2-hydroxyethylthio)imidazole is oxidized, thus obtaining 0.41 g. of 4,5-bis(4-chlorophenyl)-2-(2-hydroxyethylsulfonyl)imidazole, m.p. 191°.

EXAMPLE 13

A mixture of 4.20 g. of 4,5-bis(p-tolyl)-2-mercaptoimidazole and 2.49 g. of 2-bromoethanol in 75 ml. of absolute ethanol is heated for 4.5 hours under argon with refluxing. The solution, cooled to 5°, is neutralized by adding 2 N sodium hydroxide solution, poured into 800 ml. of ice water, and left at ice bath temperature for 45 minutes. The mixture is thus recrystallized. The crystals are vacuum-filtered, washed with water, and dried over vacuum at 60°. The crude product is recrystallized from 200 ml. of acetonitrile with the addition of a small amount of activated carbon, thus obtaining 3.95 g. of 4,5-bis(p-tolyl)-2-(2-hydroxyethylthio)imidazole, m.p. 182°.

EXAMPLE 14

Under the conditions of Example 2, 0.5 g. of 4,5-bis(p-tolyl)-2-(2-hydroxyethylthio)imidazole is oxidized, thus obtaining 0.33 g. of 4,5-bis(p-tolyl)-2-(2-hydroxyethylsulfinyl)-imidazole, m.p. 169°.

EXAMPLE 15

Under the conditions of Example 3, 0.6 g. of 4,5-bis(p-tolyl)-2-(2-hydroxyethylthio)imidazole is oxidized, thus obtaining 0.50 g. of 4,5-bis(p-tolyl)-2-(2-hydroxyethylsulfonyl)imidazole, m.p. 166°.

EXAMPLE 16

A solution of 1.25 g. of 4,5-bis(2-pyridyl)-2-mercaptoimidazole in 50 ml. of absolute ethanol is combined with 0.69 g. of 2-bromoethanol in 5 ml of absolute ethanol. The mixture is heated under reflux and under argon for 8 hours. The solvent is then evaporated under vacuum, the crystalline residue is vacuum-filtered and washed with absolute ether. Recrystallization from ethyl acetate/hexne yields 1.58 g. of 4,5-bis(2-pyridyl)-2-(2-hydroxyethylthio)imidazole, hydrobromide, m.p. 249°–250°.

EXAMPLE 17

Under the conditions of Example 2, 0.6 g. of 4,5-bis(2-pyridyl)-2-(2-hydroxyethylthio)imidazole is oxidized, thus obtaining 0.42 g. of 4,5-bis(2-pyridyl)-2-(2-hydroxyethylsulfinyl)imidazole, m.p. 215°–217°.

EXAMPLE 18

Under the conditions of Example 3, 0.5 g. of 4,5-bis(2-pyridyl)-2-(2-hydroxyethylthio)imidazole is oxidized, thus obtaining 0.43 g. of 4,5-bis(2-pyridyl)-2-(2-hydroxyethylsulfonyl)imidazole, m.p. 216°.

EXAMPLE 19

1.38 g. of 2-bromoethanol in 10 ml. of absolute ethanol is added to a suspension of 2.64 g. of 4,5-di(2-thienyl)-2-mercaptoimidazole in 50 ml. of absolute ethanol, and the mixture is heated under reflux for 8 hours under argon. The solution is allowed to cool off and neutralized with 2 N sodium hydroxide solution and then poured into 600 ml. of water. The thus-precipitated oil is taken up in ethyl acetate. The organic solution is dried over sodium sulfate and evaporated to dryness under vacuum. The residue is recrystallized from ethyl acetate, yielding 2.29 g. of 4,5-di(2-thienyl)-2-(2-hydroxyethylthio)imidazole, m.p. 125°.

EXAMPLE 20

Under the conditions of Example 2, 0.5 g. of 4,5-di(2-thienyl)-2-(2-hydroxyethylthio)imidazole is oxidized, thus obtaining 0.29 g. of 4,5-di(2-thienyl)-2-(2-hydroxyethylsulfinyl)imidazole, m.p. 98°.

EXAMPLE 21

Under the conditions of Example 3, 0.5 g. of 4,5-di(2-thienyl)-2-(2-hydroxyethylthio)imidazole is oxidized, yielding 0.42 g. of 4,5-di(2-thienyl)-2-(2-hydroxyethylsulfonyl)imidazole, m.p. 101°–103°.

EXAMPLE 22

A mixture of 6.25 g. of 4,5-bis(4-methoxyphenyl)-2-mercaptoimidazole and 3.66 g. of 2-bromopropionic acid ethyl ester in 100 ml. of absolute ethanol is heated for 2.5 hours under argon with refluxing. The cooled solution is neutralized with 2 N sodium hydroxide solution and poured into 1000 ml. of ice water. The thus-precipitated oil is taken up in ethyl acetate, the solution is dried over sodium sulfate and concentrated under vacuum, thus obtaining 7.12 g. of [4,5-bis(4-methoxyphenyl)-2-imidazolyl]-2-thiopropionic acid ethyl ester as a colorless oil.

Elementary analysis: $C_{22}H_{24}N_2O_4S$: (412.52). Calculated: C: 66.64; H: 6.10; N: 7.06; S: 8.09. Found: C: 66.41; H: 6.23; N: 7.15; S: 8.21.

EXAMPLE 23

A solution of 8.25 g. of [4,5-bis(4-methoxyphenyl)-2-imidazolyl]-2-thiopropionic acid ethyl ester in 150 ml. of absolute tetrahydrofuran is combined with 0.607 g. of lithium aluminum hydride, which latter is added in incremental portions. The mixture is stirred for 30 minutes at room temperature, decomposed with saturated ammonium chloride solution, and extracted with ethyl acetate. After drying the organic solution over sodium sulfate, the mixture is concentrated to dryness under vacuum. The crystalline residue is recrystallized from toluene, thus obtaining 5.07 g. of [4,5-bis(4-methoxyphenyl)]-2-(2-hydroxy-1-methylethylthio)imidazole, m.p. 141°.

EXAMPLE 24

At room temperature, a solution of 2.16 g. of 3-chloroperbenzoic acid in 150 ml. of chloroform is added dropwise to a solution of 3.71 g. of [4,5-bis(4-methoxyphenyl)]-2-(2-hydroxy-1-methylethylthio)imidazole in 200 ml. of chloroform. The mixture is stirred overnight at room temperature and washed with saturated sodium bicarbonate solution. The organic solution is dried over sodium sulfate and concentrated under vacuum. The residue is purified by chromatography on 200 g. of silica gel with ethyl acetate as the eluent. After evaporation of the solvent, 2.67 g. of [4,5-bis(4-methoxyphenyl)]-2-(2-hydroxy-1-methylethylsulfinyl)imidazole is obtained as an amorphous foam.

$C_{20}H_{22}N_2O_4S$: (386.47). Calculated: C: 62.16; H: 5.74; N: 7.25; S: 8.30. Found: C: 62.40; H: 5.82; N: 7.19; S: 8.22.

EXAMPLE 25

At room temperature, a solution of 5.20 g. of 3-chloroperbenzoic acid in 250 ml. of chloroform is added dropwise to a solution of 3.71 g. of [4,5-bis(4-methoxyphenyl)]-2-(2-hydroxy-1-methylethylthio)imidazole in 200 ml. of chloroform. The mixture is stirred overnight at room temperature, then washed with saturated sodium bicarbonate solution; the organic solution is dried over sodium sulfate and concentrated to dryness under vacuum, thus obtaining 3.70 g. of [4,5-bis(4-methoxyphenyl)]-2-(2-hydroxy-1-methylethyl-sulfonyl)imidazole as an amorphous foam, m.p. 68°.

$C_{20}H_{22}N_2O_5S$: (402.47). Calculated: C: 59.69; H: 5.51; N: 6.96; S: 7.97. Found: C: 59.51; H: 5.61; N: 7.08; S: 7.88.

EXAMPLE 26

A mixture of 9.36 g. of 4,5-bis(4-methoxyphenyl)-2-mercaptoimidazole and 9.13 g. of the ethyl ester of 2-bromoisobutyric acid in 150 ml. of ethanol is heated under reflux for 6 hours under argon. The cooled solution is neutralized with 2 N sodium hydroxide solution, poured into 600 ml. of ice water, and the crude product is extracted with dichloromethane. The organic solution is dried over sodium sulfate and concentrated to dryness under vacuum. The residue is crystallized from dichloromethane/diethyl ester, thus obtaining 11.29 g. of [4,5-bis(4-methoxyphenyl)-2-imidazolyl]-2-methyl-2-thiopropionic acid ethyl ester, m.p. 115°.

EXAMPLE 27

8.53 g. of [4,5-bis(4-methoxyphenyl)-2-imidazolyl]-2-methyl-2-thiopropionic acid ethyl ester is dissolved in a mixture of respectively 75 ml. of absolute tetrahydrofuran and diethyl ether and combined in incremental portions with a total of 570 mg. of lithium aluminum hydride. The mixture is stirred at room temperature for 30 minutes, decomposed with saturated ammonium chloride solution, and extracted with ethyl acetate. After drying the organic solution over sodium sulfate, the mixture is concentrated to dryness under vacuum. Crystallization from toluene yields 6.33 g. of 4,5-bis(4-methoxyphenyl)-2-(1,1-dimethyl-2-hydroxyethylthio)imidazole, m.p. 195°.

EXAMPLE 28

Under the conditions of Example 2, 3.81 g. of 4,5-bis(4-methoxyphenyl)-2-(1,1-dimethyl-2-hydroxyethyl-thio)-imidazole is oxidized, thus obtaining 2.67 g. of 4,5-bis(4-methoxyphenyl)-2-(1,1-dimethyl-2-hydroxyethylsulfinyl)imidazole, m.p. 215°.

EXAMPLE 29

Under the conditions of Example 3, 3.81 g. of 4,5-bis(4-methoxyphenyl)-2-(1,1-dimethyl-2-hydroxyethylthio)imidazole is oxidized, thus obtaining 3.22 g. of 4,5-bis(4-methoxyphenyl)-2-(1,1-dimethyl-2-hydroxyethylsulfonyl)imidazole, m.p. 187°.

EXAMPLE 30

A solution of 3.95 g. of 4,5-bis(4-methoxyphenyl)-2-mercaptoimidazole in 100 ml. of absolute methanol, wherein 320 mg. of sodium have been dissolved, is combined with 2.14 g. of 2-bromobutyrolactone in 30 ml. of absolute methanol, and the mixture is heated under reflux for 2.5 hours under argon. After cooling, the solution is poured into 500 ml. of ice water and neutralized with 2 N sulfuric acid. The product is extracted with ethyl acetate; the organic solution is dried over sodium sulfate and concentrated under vacuum. The residual oil is made to crystallize from tetrahydrofuran/hexane, thus obtaining 1.23 g. of [4,5-bis(4-methoxyphenyl)-2-imidazolyl]-2-thiobutyrolactone, m.p. 140°–142°.

EXAMPLE 31

A solution of 3.96 g. of [4,5-bis(4-methoxyphenyl)-2-imidazolyl]-2-thiobutyrolactone in 100 ml. of absolute tetrahydrofuran is combined with 300 mg. of lithium aluminum hydride. The mixture is stirred for 30 minutes at room temperature, decomposed with saturated ammonium chloride solution, and extracted with ethyl acetate. After drying the organic solution over sodium sulfate, it is concentrated to dryness under vacuum, thus obtaining 3.26 g. of [4,5-bis(4-methoxyphenyl)-2-imidazolyl]-2-thio-1,4-butanediol in the form of a viscous oil.

$C_{21}H_{24}N_2O_4S$: (400.50). Calculated: C: 62.98; H: 6.04; N: 7.00; S: 8.01. Found: C: 62.71; H: 6.13; N: 6.89; S: 8.17.

EXAMPLE 32

A solution of 6.25 g. of 4,5-bis(4-methoxyphenyl)-2-mercaptoimidazole in 50 ml. of absolute dimethylformamide is combined with 0.96 g. of 50% sodium hydride, and the mixture is agitated for 30 minutes at 60°. Then, 2.74 g. of chloroacetaldehyde dimethyl acetal in 20 ml. of absolute dimethylformamide is added to the reaction mixture, and the latter is stirred for 4 hours under argon at 80°. The cooled-off solution is poured into 700 ml. of water and extracted with chloroform. The organic solution is dried over sodium sulfate, concentrated to dryness under vacuum, and the dark-brown residue is purified by chromatography on 500 g. of silica gel. Elution with ethyl acetate/hexane in a ratio of 1:3 yields 5.01 g. of 4,5-bis(4-methoxyphenyl)-2-(2,2-dimethoxyethylthio)imidazole as a light-yellow oil.

$C_{21}H_{24}N_2O_4S$: (400.50). Calculated: C: 62.98; H: 6.04; N: 7.00; S: 8.01. Found: C: 62.69; H: 6.16; N: 7.08; S: 8.11.

EXAMPLE 33

A solution of 1.19 g. of 3-chloroperbenzoic acid in 100 ml. of dichloromethane is added dropwise to a solution of 2.0 g. of 4,5-bis(4-methoxyphenyl)-2-(2,2-dimethoxyethylthio)imidazole in 150 ml. of dichloromethane, and the mixture is agitated for 4 hours at room temperature. The mixture is then washed with sodium bicarbonate solution; the organic solution is dried over sodium sulfate and concentrated to dryness under vacuum. The residue is crystallized from ethyl acetate/hexane. Recrystallization from ethyl acetate/ethanol yields 1.52 g. of 4,5-bis(4-methoxyphenyl)-2-(2,2-dimethoxyethylsulfinyl)imidazole, m.p. 127°-128°.

EXAMPLE 34

A solution of 2.97 g. of 3-chloroperbenzoic acid in 100 ml. of dichloromethane is added dropwise to a solution of 2.5 g. of 4,5-bis(4-methoxyphenyl)-2-(2,2-dimethoxyethylthio)-imidazole in 150 ml. of dichloromethane, and the mixture is agitated overnight at room temperature. Then the mixture is washed with sodium bicarbonate solution; the organic solution is dried over sodium sulfate and concentrated to dryness under vacuum. The residue is crystallized from ethyl acetate/hexane. Recrystallization from ethanol/ether yields 1.96 g. of 4,5-bis(4-methoxyphenyl)-2-(2,2-dimethoxyethylsulfonyl)-imidazole, m.p. 78°-80°.

EXAMPLE 35

A solution of 12.48 g. of 4,5-bis(4-methoxyphenyl)-2-mercaptoimidazole in 150 ml. of absolute dimethylformamide is combined with 1.92 g. of 50% sodium hydride. After 30 minutes of agitation at 60°, the mixture is combined with 7.35 g. of bromoacetaldehyde ethylene ketal in 40 ml. of absolute dimethylformamide, and the mixture is stirred under argon for 4 hours at 90°. The cooled solution is poured into 1000 ml. of water, the thus-separated oil is taken up in ethyl acetate; the organic solution is dried over sodium sulfate and concentrated to dryness under vacuum. The residue is recrystallized from ethyl acetate, thus obtaining 11.65 g. of [4,5-bis(4-methoxyphenyl)-2-imidazolyl]-1,3-dioxolan-2-ylmethyl)sulfide, m.p. 118°-119°.

EXAMPLE 36

1.19 g (80%) of 3-chloroperbenzoic acid in 100 ml. of dichloromethane is added dropwise to a solution of 1.99 g. of [4,5-bis(4-methoxyphenyl)-2-imidazolyl]-(1,3-dioxolan-2-ylmethyl)sulfide in 150 ml. of dichloromethane. The mixture is stirred for 4 hours at room temperature, then washed with sodium bicarbonate solution; the organic solution is dried over sodium sulfate and concentrated under vacuum. The residue is crystallized from ethyl acetate/hexane. After recrystallization from ethyl acetate/hexane, 1.43 g. of [4,5-bis-(4-methoxyphenyl)-2-imidazolyl]-(1,3-dioxolan-2-ylmethyl)-sulfoxide is obtained, m.p. 203°-204°.

EXAMPLE 37

A solution of 2.38 g. (80%) of 3-chloroperbenzoic acid in 150 ml. of dichloromethane is added dropwise to a solution of 1.99 g. of [4,5-bis(4-methoxyphenyl)-2-imidazolyl]-(1,3-dioxolan-2-ylmethyl)sulfide in 150 ml. of dichloromethane. The mixture is agitated overnight at room temperature, then washed with sodium bicarbonate solution, and the organic solution is dried over sodium sulfate and concentrated under vacuum. The residue is crystallized from ethyl acetate/ethanol. Recrystallization from ethyl acetate/ethanol yields 1.71 g. of [4,5-bis(4-methoxyphenyl)-2-imidazolyl]-(1,3-dioxolan-2-yl-methyl)sulfone, m.p. 150°.

EXAMPLE 38

Under agitation, 3.95 g. of 4,5-bis(4-methoxyphenyl)-2-mercaptoimidazole is added to a solution of 320 mg. of sodium in 100 ml. of absolute methanol. The clear, yellow solution is combined with a solution of 2.53 g. of bromoacetaldehyde diethyl acetal in 30 ml. of absolute methanol. The mixture is heated for 48 hours under argon with refluxing, is then cooled, and poured into 600 ml. of ice water. The product is extracted with ethyl acetate. The organic solution is dried over sodium sulfate and concentrated to dryness under vacuum. Unreacted imidazole is removed by crystallization from acetone/hexane. The mother liquor is then stirred into hexane. The thus-precipitated oil is separated and dried under an oil pump vacuum at 50°, thus producing 2.93 g. of 4,5-bis-(4-methoxyphenyl)-2-(2,2-diethoxyethylthio)imidazole as a yellowish, viscous oil.

$C_{23}H_{28}N_2O_4S$: (428.55). Calculated: C: 64.46; H: 6.58; N: 6.54; S: 7.48. Found: C: 64.49; H: 6.69; N: 6.48; S: 7.22.

EXAMPLE 39

0.96 g. of 50% sodium hydride is added to a solution of 6.24 g. of 4,5-bis(4-methoxyphenyl)-2-mercaptoimidazole in 100 ml. of absolute dimethylformamide, and the mixture is heated to 60° for 30 minutes. Then the mixture is combined with a solution of 4.33 g. of bromoacetaldehyde diethyl acetal in 20 ml. of absolute dimethylformamide and stirred for 4 hours at 80° under argon. The mixture is then allowed to cool, poured into 800 ml. of ice water, and extracted with chloroform. The organic solution is dried over sodium sulfate and concentrated to dryness under vacuum. The residue is treated as described in Example 39, thus obtaining 6.53 g. of 4,5-bis-(4-methoxyphenyl)-2-(2,2-diethoxyethylthio)imidazole as a yellow oil.

$C_{23}H_{28}N_2O_4S$: (428.55). Calculated: C: 64.46; H: 6.58; N: 6.54; S: 7.48. Found: C: 64.53; H: 6.68; N: 6.57; S: 7.31.

EXAMPLE 40

At room temperature, 2.38 g. (80%) of 3-chloroperbenzoic acid in 150 ml. of methylene chloride is added dropwise to a solution of 4.29 g. of 4,5-bis(4-methoxyphenyl)-2-(2,2-diethoxyethylthio)imidazole in 150 ml. of methylene chloride. The mixture is stirred for 2 hours at room temperature and washed with sodium bicarbonate solution. The organic solution is dried over sodium sulfate and concentrated under vacuum. The remaining oil is taken up in diethyl ether and made to crystallize by adding diisopropyl ether, thus obtaining 3.49 g. of 4,5-bis(4-methoxyphenyl)-2-(2,2-diethoxyethylsulfinyl)imidazole, m.p. 173°–174°.

EXAMPLE 41

At room temperature, 4.76 g. (80%) of 3-chloroperbenzoic acid in 150 ml. of methylene chloride is added dropwise to a solution of 4.29 g. of 4,5-bis(4-methoxyphenyl)-2-(2,2-diethoxyethylthio)imidazole in 150 ml. of methylene chloride. The mixture is stirred at room temperature for 1.5 hours and washed with sodium bicarbonate solution. The organic solution is dried over sodium sulfate and concentrated under vacuum. The remaining oil is treated as described in Example 40, thus producing 3.09 g. of 4,5-bis(4-methoxyphenyl)-2-(2,2-diethoxyethylsulfonyl)imidazole, m.p. 149°–150°.

EXAMPLE 42

A solution of 3.95 g. of 4,5-bis(4-methoxyphenyl)-2-mercaptoimidazole in 100 ml. of absolute methanol, wherein 320 mg. of sodium have been dissolved, is combined with 2.53 g. of 3-chloropropanol, and the mixture is heated under reflux for 24 hours under an argon atmosphere. The cooled solution is poured into 500 ml. of water, neutralized with 2 N sulfuric acid, and extracted with chloroform. The organic solution is dried over sodium sulfate, concentrated to dryness under vacuum, and the residue is crystallized from ethanol, yielding 2.98 g. of 4,5-bis(4-methoxyphenyl)-2-(3-hydroxypropylthio)imidazole, m.p. 163°.

EXAMPLE 43

Under agitation, 6.24 g. of 4,5-bis(4-methoxyphenyl)-2-mercaptoimidazole is added to a solution of 506 mg. of sodium in 150 ml. of absolute ethanol. The clear, yellow solution is then combined with a solution of 1.24 g. of propylene oxide in 40 ml. of absolute ethanol. The mixture is stirred under argon for 2 hours at room temperature, then poured into 600 ml. of ice water. The precipitated crystals are vacuum-filtered, washed with water, and dried under vacuum at 70°, thus obtaining 5.89 g. of 4,5-bis(4-methoxyphenyl)-2-(2-hydroxypropylthio)imidazole, m.p. 163°.

EXAMPLE 44

Under agitation, 6.24 g. of 4,5-bis(4-methoxyphenyl)-2-mercaptoimidazole is added to a solution of 483 mg. of sodium in 100 ml. of absolute ethanol. The clear, yellow solution is then combined with a solution of 1.59 g. of isobutene oxide in 30 ml. of absolute ethanol, and the mixture is stirred for 3 hours under argon at room temperature. Then the mixture is poured into 600 ml. of ice water, the precipitated crystals are vacuum-filtered, washed with water, and dried under vacuum at 70°. Recrystallization from benzene yields 6.57 g. of 4,5-bis(4-methoxyphenyl)-2-(2-hydroxy-2-methylpropylthio)imidazole, m.p. 185°.

EXAMPLE 45

3.12 g. of 4,5-bis(4-methoxyphenyl)-2-mercaptoimidazole is dissolved in a mixture of 40 ml. of dioxane and 40 ml. of tetrahydrofuran and then combined with 1.08 g. of the ethyl ester of propiolic acid in 10 ml. of dioxane. After adding 1 ml. of 1 N sodium hydroxide solution, the mixture is stirred for 10 minutes under argon. Thereafter the mixture is poured into 500 ml. of ice water, extracted with chloroform; the organic solution is dried over sodium sulfate and concentrated to dryness under vacuum. The residue is crystallized from ether/hexane. Recrystallization from ethyl acetate/hexane yields 3.14 g. of [4,5-bis(4-methoxyphenyl)-2-imidazolyl]-3-thiopropenoic acid ethyl ester, m.p. 206°.

EXAMPLE 46

1.25 g. of 2-bromoethanol in 50 ml. of ethanol is added to a solution of 2.95 g. of 4(5)-(4-dimethylaminophenyl)-5(4)-phenyl-2-mercaptoimidazole in 100 ml. of dimethylformamide. The mixture is stirred for 3 hours at 75° under argon, is then allowed to cool, and is neutralized with 2 N sodium hydroxide solution. The solution is introduced into 1000 ml. of ice water and extracted with ethyl acetate. The organic solution is dried over sodium sulfate and concentrated to dryness under vacuum. The residue is filtered over 200 g. of silica gel with ethyl acetate/hexane 8:2. The concentrated eluate is crystallized from ethyl acetate/hexane. Yield: 2.37 g. of 4-(4-dimethylaminophenyl)-5-phenyl-2-(2-hydroxyethylthio)imidazole, m.p. 135°–137°.

EXAMPLE 47

A mixture of 7.81 g. of 4,5-bis(4-methoxyphenyl)-2-mercaptoimidazole and 4.87 g. of 2-bromoethyl methyl ether is heated under reflux for 3 hours in 150 ml. of ethanol. The mixture is allowed to cool, neutralized with 2 N sodium hydroxide solution, and poured into 1200 ml. of ice water. The thus-precipitated crystals are vacuum-filtered, washed with water, and dried under vacuum at 50°. The crude product is recrystallized from ethyl acetate, thus obtaining 6.37 g. of 4,5-bis(4-methoxyphenyl)-2-(2-methoxyethylthio)imidazole, m.p. 139°.

EXAMPLE 48

One drop of $H_2SO_4$ in 1 ml. of absolute tetrahydrofuran is introduced into a cooled solution of 3.12 g. of 4,5-bis(4-methoxyphenyl)-2-(2-hydroxyethylthio)imidazole and 0.7 g. of methyl vinyl ether in 150 ml. of absolute tetrahydrofuran. The mixture is stirred in a sealed vessel overnight at room temperature, then combined with powdered calcium carbonate, stirred for another 30 minutes, diluted with tetrahydrofuran, and the solid matter is filtered off. The filtrate is concentrated to dryness under vacuum, thus obtaining 3.53 g. of 2-[4,5-bis(4-methoxyphenyl)imidazol-2-ylthio]-1'-methoxy diethyl ether as a colorless oil.

$C_{22}H_{26}N_2O_4S$: (414.53). Calculated: C: 63.75; H: 6.32; N: 6.76; S: 7.74. Found: C: 63.68; H: 6.41; N: 6.67; S: 7.66.

EXAMPLE 49

1.12 g. of propargyl alcohol and 300 mg. of copper-(II) chloride are added to a solution of 6.24 g. of 4,5-bis(4-methoxyphenyl)-2-mercaptoimidazole in 50 ml. of dimethylformamide. The mixture is heated for 12 hours to 120° under argon, then cooled, stirred into ammoniacal ice water, and the product is extracted with ether. The organic solution is dried over sodium sulfate and concentrated to dryness under vacuum, thus obtaining 4.13 g. of 4,5-bis(4-methoxyphenyl)-2-(3-hydroxy-1-propenylthio)imidazole as an amorphous foam.

$C_{20}H_{20}N_2O_3S$: (368.46). Calculated: C: 65.20; H: 5.47; N: 7.60; S: 8.70. Found: C: 65.10; H: 5.58; N: 7.49; S: 8.62.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An imidazole derivative of the formula

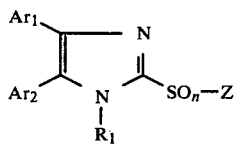

wherein

Ar$_1$ and Ar$_2$ are each phenyl; phenyl substituted by halogen, $C_{1-4}$ alkyl, $C_{1-4}$ alkoxy or $C_{2-6}$ dialkylamino; with the proviso that Ar$_1$ and Ar$_2$ are not both unsubstituted phenyl;

R$_1$ is hydrogen, $C_{1-4}$ alkyl or $C_{1-4}$ alkyl substituted by hydroxy, $C_{1-4}$ alkoxy or $C_{1-6}$ alkanoyloxy;

n is 0, 1 or 2; and

Z is a $C_{2-6}$-alkenyl residue substituted by one or two of hydroxy, $C_{1-4}$ alkoxy, $C_{2-8}$ alkylenedioxy, $C_{1-6}$ alkanoyloxy or benzoyloxy, or by one alkoxycarbonyl group; or $C_{1-6}$ alkyl substituted by two hydroxy or by one or two of $C_{1-4}$ alkoxy; $C_{2-8}$ alkylenedioxy; $C_{1-6}$ alkanoyloxy or benzoyloxy;

and the salts thereof with physiologically acceptable acids.

2. An imidazole derivative of claim 1, wherein Ar$_1$ and Ar$_2$ are each phenyl; phenyl substituted in the para position by fluorine, chlorine, alkyl of 1–4 carbon atoms, alkoxy of 1–4 carbon atoms or dialkylamino of 2–6 carbon atoms.

3. An imidazole derivative of claim 2, wherein Ar$_1$ and Ar$_2$ are each phenyl, 4-fluorophenyl, 4-chlorophenyl, 4-methylphenyl, 4-methoxyphenyl, 4-dimethylaminophenyl.

4. An imidazole derivative of claim 1, wherein R$_1$ is hydrogen, alkyl of 1–4 carbon atoms, 2-hydroxyethylene or 2-$C_{1-6}$-alkanoyloxyethylene.

5. An imidazole derivative of claim 1, wherein n is 1 or 2.

6. An imidazole derivative of claim 1, wherein Z is a $C_{2-6}$-alkyl or $C_{2-6}$-alkenyl residue substituted by two hydroxy groups attached to different carbon atoms; by $C_{1-4}$ alkoxy; by $C_{1-6}$ alkanoyloxy; or by benzolyoxy; or $C_{2-6}$ alkenyl substituted by one hydroxy.

7. An imidazole derivative of claim 1, wherein Z is a $C_{1-3}$-alkyl or -alkenyl residue substituted by 1,3-dioxolan-2-yl or by a dialkoxymethylene group of 1–4 carbon atoms in each alkoxy group.

8. An imidazole derivative of claim 1, wherein Z is a $C_{2-3}$-alkenyl residue substituted by a $C_{1-4}$ alkoxy-carbonyl group.

9. O-Acetylglycolic acid {2-[4,5-bis(4-methoxyphenyl)-2-imidazolylthio]ethyl} ester hydrochloride.

10. 4,5-Bis(4-methoxyphenyl)-2-(2-acetoxyethylthio)imidazole, a compound of claim 1.

11. [4,5-Bis(4-methoxyphenyl)-2-imidazolyl]-2-thio-1,4-butanediol, a compound of claim 1.

12. 4,5-Bis(4-methoxyphenyl)-2-(2,2-dimethoxyethylthio)imidazole, a compound of claim 1.

13. 4,5-Bis(4-methoxyphenyl)-2-(2,2-dimethoxyethylsulfinyl)imidazole, a compound of claim 1.

14. 4,5-Bis(4-methoxyphenyl)-2-(2,2-dimethoxyethylsulfonyl)imidazole, a compound of claim 1.

15. [4,5-Bis(4-methoxyphenyl)-2-imidazolyl]-(1,3-dioxolan-2-ylmethyl)sulfide, a compound of claim 1.

16. [4,5-Bis(4-methoxyphenyl)-2-imidazolyl]-(1,3-dioxolan-2-ylmethyl)sulfoxide, a compound of claim 1.

17. [4,5-Bis(4-methoxyphenyl)-2-imidazolyl]-(1,3-dioxolan-2-ylmethyl)sulfone, a compound of claim 1.

18. 4,5-Bis(4-methoxyphenyl)-2-(2,2-diethoxyethylthio)imidazole, a compound of claim 1.

19. 4,5-Bis(4-methoxyphenyl)-2-(2,2-diethoxyethylsulfinyl)imidazole, a compound of claim 1.

20. 4,5-Bis(4-methoxyphenyl)-2-(2,2-diethoxyethylsulfonyl)imidazole, a compound of claim 1.

21. [4,5-Bis(4-methoxyphenyl)-2-imidazolyl]-3-thiopropenoic acid ethyl ester, a compound of claim 1.

22. 4,5-Bis(4-methoxyphenyl)-2-(3-hydroxy-1-propenylthio)imidazole, a compound of claim 1.

23. A pharmaceutical composition comprising an antiinflammatorily effective amount of a compound of claim 1 and a pharmaceutically acceptable carrier.

24. A method of treating inflammation in a mammal which comprises administering an antiinflammatorily effective amount of a compound of claim 1.

* * * * *